(12) United States Patent
Sanborn et al.

(10) Patent No.: US 10,729,848 B2
(45) Date of Patent: Aug. 4, 2020

(54) FORCE SENSING DEVICES, SYSTEMS AND METHODS FOR SYRINGE PUMPS

(71) Applicant: Smiths Medical ASD, Inc., Plymouth, MN (US)

(72) Inventors: Jonathan Sanborn, St. Louis Park, MN (US); John P. Rukavina, Chanhassen, MN (US); Grant A. Adams, Anoka, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 272 days.

(21) Appl. No.: 15/735,863

(22) PCT Filed: Jun. 17, 2016

(86) PCT No.: PCT/US2016/037967
§ 371 (c)(1),
(2) Date: Dec. 12, 2017

(87) PCT Pub. No.: WO2016/205584
PCT Pub. Date: Dec. 22, 2016

(65) Prior Publication Data
US 2018/0177944 A1 Jun. 28, 2018

Related U.S. Application Data

(60) Provisional application No. 62/180,938, filed on Jun. 17, 2015.

(51) Int. Cl.
*A61M 5/168* (2006.01)
*A61M 5/145* (2006.01)

(52) U.S. Cl.
CPC ........ *A61M 5/16831* (2013.01); *A61M 5/145* (2013.01); *A61M 5/1452* (2013.01);
(Continued)

(58) Field of Classification Search
CPC ............... A61M 5/142; A61M 5/1452; A61M 5/16831; A61M 5/1458; A61M 5/1456; A61M 2205/332
See application file for complete search history.

(56) References Cited

U.S. PATENT DOCUMENTS

3,630,417 A 12/1971 De Haas
4,185,759 A 1/1980 Zissimopoulos
(Continued)

FOREIGN PATENT DOCUMENTS

CN 101371127 A 2/2009
CN 102114282 A 7/2011
(Continued)

OTHER PUBLICATIONS

International Search Report for corresponding International Application No. PCT/US2016/037967 dated Sep. 12, 2016; 5 pages.
(Continued)

*Primary Examiner* — Laura A Bouchelle
(74) *Attorney, Agent, or Firm* — Patterson Thuente Pedersen, P.A.

(57) ABSTRACT

A syringe pump configured to mechanically align a force sensor with an axis of a plunger of a syringe for a purpose of minimizing force measurement inaccuracies. The syringe pump includes a syringe pump housing that is configured to receive at least a portion of said syringe, wherein the syringe is selected from a plurality of syringes of different dimensions. A plunger retainer mechanism is pivotably coupled to the syringe pump housing and is configured to retain said plunger of said syringe. The plunger retainer mechanism pivots relative to the syringe pump housing based on a sensed dimension of the plunger to align a force sensor coupled to the plunger retainer mechanism with the axis of the plunger; and a syringe drive mechanism is operably coupled to the syringe pump housing and configured to shift
(Continued)

the plunger relative to the portion of the syringe received by the syringe pump housing.

15 Claims, 6 Drawing Sheets

(52) U.S. Cl.
CPC ...... *A61M 5/1458* (2013.01); *A61M 5/16859* (2013.01); *A61M 2005/16863* (2013.01); *A61M 2205/332* (2013.01); *A61M 2205/502* (2013.01)

(56) References Cited

U.S. PATENT DOCUMENTS

| | | | |
|---|---|---|---|
| 4,236,880 A | 12/1980 | Archibald | |
| 4,336,800 A | 6/1982 | Pastrone | |
| 4,544,369 A | 10/1985 | Skakoon et al. | |
| 4,747,828 A | 5/1988 | Tseo | |
| 4,762,518 A | 8/1988 | Kreinick | |
| 4,804,368 A | 2/1989 | Skakoon et al. | |
| 4,976,151 A | 12/1990 | Morishita | |
| 4,978,335 A | 12/1990 | Arthur, III | |
| 5,034,004 A | 7/1991 | Crankshaw | |
| 5,232,449 A | 8/1993 | Stern et al. | |
| 5,295,967 A | 3/1994 | Rondelet et al. | |
| 5,395,320 A | 3/1995 | Padda et al. | |
| 5,399,171 A | 3/1995 | Bowman et al. | |
| 5,501,665 A | 3/1996 | Jhuboo et al. | |
| 5,647,853 A | 7/1997 | Feldmann et al. | |
| 5,695,473 A | 12/1997 | Olsen | |
| 5,814,015 A | 9/1998 | Gargano et al. | |
| 5,935,106 A | 8/1999 | Olsen | |
| 5,989,222 A | 11/1999 | Cole et al. | |
| 6,475,180 B2 | 11/2002 | Peterson et al. | |
| 6,551,277 B1* | 4/2003 | Ford .................. | A61M 5/1456 340/540 |
| 7,150,724 B2 | 12/2006 | Morris et al. | |
| 7,635,349 B2 | 12/2009 | Tribe et al. | |
| 8,262,616 B2 | 9/2012 | Grant et al. | |
| 8,876,793 B2 | 11/2014 | Ledford et al. | |
| 9,119,917 B2 | 9/2015 | Blomquist | |
| 9,173,998 B2 | 11/2015 | Rosinko et al. | |
| 10,004,847 B2 | 6/2018 | Wander et al. | |
| 2002/0045861 A1 | 4/2002 | Tribe | |
| 2002/0077852 A1 | 6/2002 | Ford et al. | |
| 2003/0069559 A1 | 4/2003 | Platt et al. | |
| 2003/0205587 A1 | 11/2003 | Tribe et al. | |
| 2003/0229311 A1 | 12/2003 | Morris et al. | |
| 2003/0233069 A1 | 12/2003 | Gillespie et al. | |
| 2004/0073161 A1 | 4/2004 | Tachibana | |
| 2005/0096593 A1 | 5/2005 | Pope et al. | |
| 2005/0234387 A1 | 10/2005 | Tonelli et al. | |
| 2007/0244469 A1 | 10/2007 | Ozeri et al. | |
| 2009/0270833 A1 | 10/2009 | DeBelser et al. | |
| 2010/0214110 A1 | 8/2010 | Wang et al. | |
| 2010/0262078 A1 | 10/2010 | Blomquist | |
| 2013/0129532 A1 | 5/2013 | Flachbart et al. | |
| 2014/0107609 A1 | 4/2014 | Blomquist | |
| 2014/0276537 A1 | 9/2014 | Kruse | |
| 2015/0133890 A1 | 5/2015 | Wander et al. | |
| 2016/0051758 A1 | 2/2016 | Rosinko et al. | |
| 2018/0169329 A1 | 6/2018 | Wander et al. | |

FOREIGN PATENT DOCUMENTS

| | | |
|---|---|---|
| JP | S59-97671 | 6/1984 |
| JP | 06-190036 A | 7/1994 |
| JP | 2008-264140 A | 11/2008 |
| WO | WO 2009/113341 A1 | 9/2009 |
| WO | WO 2011009224 A2 | 1/2011 |
| WO | WO 2011/093103 A1 | 8/2011 |
| WO | WO 2012/040528 A1 | 3/2012 |
| WO | WO 2013/177379 A1 | 11/2013 |
| WO | WO 2014/100658 A1 | 6/2014 |

OTHER PUBLICATIONS

Written Opinion of the International Searching Authority for corresponding International Application No. PCT/US2016/037967 dated Sep. 12, 2016; 5 pages.
Office Action dated Mar. 1, 2017 for Japanese Application No. 2015-514175, 8 pages.
Patent Examination Report No. 1 dated Oct. 15, 2016 for Australian Application No. 2013266278, 2 pages.
International Search Report dated Aug. 28, 2013 for PCT/US2013/042388, 4 pages.
Search Report dated Oct. 13, 2015 for EP Application No. EP13794119, 7 pages.
PCT Notification Concerning Transmittal of International Preliminary Report on Patentability, International Preliminary Report on Patentability, and Written Opinion of the International Searching Authority dated Dec. 4, 2014 for PCT/US2013/042388, 8 pages.
Office Action dated Mar. 1, 2016 for Chinese Application No. 201380027501.2, 7 pages.
Office Action dated Feb. 6, 2018 for Japanese Application No. 2015514175, 7 pages.
Application and File history for U.S. Appl. No. 14/400,509, filed Nov. 11, 2014. Inventors: Wander et al.
Application and File history for U.S. Appl. No. 15/889,912, filed Feb. 6, 2018. Inventors: Wander et al.

* cited by examiner

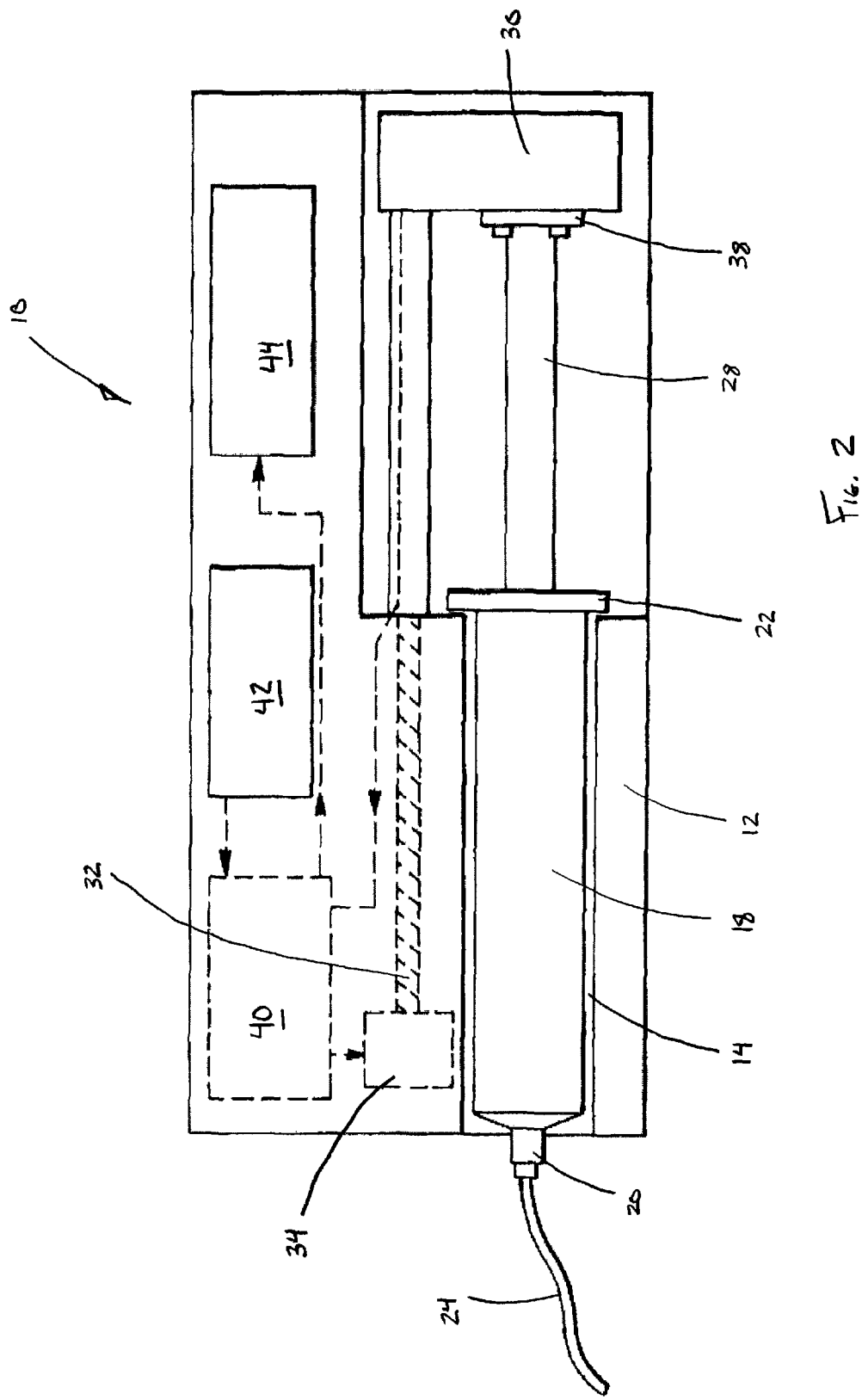

FORCE SENSING DEVICES, SYSTEMS AND METHODS FOR SYRINGE PUMPS

CROSS-REFERENCE TO RELATED APPLICATIONS

The present application is a National Phase entry of PCT Application No. PCT/US2016/037967, filed on Jun. 17, 2016, which claims priority to U.S. Provisional Patent Application No. 62/180,938, filed on Jun. 17, 2015, which are hereby fully incorporated herein by reference.

TECHNICAL FIELD

The present disclosure relates generally to medical devices. More particularly, the present disclosure relates to force sensing devices, systems, and methods for syringe pumps.

BACKGROUND

Medical infusion pumps are used in a variety of medical therapies and treatments to administer drugs, nutritional compositions, and prescribed fluids or fluid-like substances (collectively, "medicaments" or "infusates") to patients in volume- and time-controlled doses. Medicaments can be accurately and continuously administered by such pumps, at infusion rates typically ranging from as low as 0.1 ml/hr to as much as 1200 ml/hr. Because of their ability to deliver medicaments in a precise, accurate, and continuous manner, the types of medical infusion pumps commonly referred to as syringe pumps are well-suited to pain management and palliative care, for instance, and are also often useful in neonatal and pediatric intensive care units.

In operation, a medicament syringe includes a plunger that slideably, but tightly, fits inside of a cylindrical barrel which in turn contains a medicament. Medicament is administered from the cylindrical barrel by shifting the plunger through the cylindrical barrel. Medicament is thus expelled from the cylindrical barrel under pressure, through a delivery route comprising a needle, nozzle, tubing, or the like, directing the medicament to a patient. When a syringe is installed in a syringe pump, the plunger of the syringe in the pump can be acted upon by a plunger driver of the pump that functions to controllably expel medicament from the syringe for delivery to the patient as aforementioned. Medicament from a syringe in a syringe pump can be administered, for example, intravenously, intra-arterially, epidurally or subcutaneously. As will be appreciated, a constant and metered application of medicament requires a steady and accurate flow from the syringe in the syringe pump through the delivery route or path to the patient.

During the course of delivering the medicament to the patient, it is possible for an occlusion to arise in the delivery path. Examples of occlusions can include a closed stopcock, slider valve or pinched line or tubing leading to the patient. Such a condition, if undetected, can cause injury to the patient. That is, when an occlusion occurs along the delivery path, medicament may not be delivered to the patient even though the syringe pump apparently continues to function. Thus, an occlusion prevents the syringe pump from delivering medicament to the patient until the occlusion can be detected and cleared from the infusion path. For this reason, the rapid detection of occlusions along the delivery path is important to reliable syringe pump operation.

An occlusion in the infusion line can cause a force, or pressure, in the syringe to increase. In turn, force between the plunger driver of the syringe pump and the plunger can increase. A force sensor can be placed in communication with the plunger driver, as shown, for example, in U.S. Pat. Nos. 7,635,349, 6,551,277, and 8,876,793, and in U.S. Patent App. Publ. No. 2015/0133890, each of which are incorporated by reference herein. A build up of pressure beyond normative operating ranges can accordingly be sensed, triggering alarms and initiating corrective action.

Many syringe pumps are capable of accommodating a range of syringe diameters or sizes (e.g., 1 ml through 60 ml capacities). Such a pump is disclosed, for example in the aforementioned U.S. Patent App. Publ. No. 2015/0133890 (U.S. application Ser. No. 14/400,509) that is incorporated by reference herein. But in many syringe pumps, generally the plunger driver and force sensor can experience varying occlusion force vectors depending upon which particular size of syringe is being used in the syringe pump, leading to varying accuracy and responsiveness overall in the pump's occlusion sensing system. One source of inaccuracy arises from misalignment of the force sensor with an axis of the plunger in the syringe. In particular, the force sensor may be aligned with the plunger in some syringe diameters or sizes when installed in the pump; but such desirable alignment of the force sensor with the plunger of the syringe might not occur when a syringe of another diameter or size is installed in the pump. Consequently, providing axial alignment of the force sensor with the axis of the plunger, or compensating for misalignment thereof, can provide improvement in the accuracy of force measurement.

A syringe pump that is capable of aligning the force sensor with the axis of a plunger of a syringe installed in the pump, across a range of syringe diameters or sizes, would therefore provide a distinct advantage in minimizing force measurement inaccuracy.

SUMMARY OF THE DISCLOSURE

Embodiments of the present disclosure meet a need of the industry for force sensing devices, systems, and methods for syringe pumps that provide axial alignment of the force sensor with an axis of the plunger, or compensating for misalignment thereof.

In an embodiment, a syringe pump includes a force sensor with an articulating plunger retainer mechanism, wherein the plunger retainer mechanism can be positioned to align the force sensor with the axis of a plunger of a syringe from a range of syringe diameters or sizes for the purpose of minimizing force measurement inaccuracies. In addition to improving accuracy, by aligning the force sensor with the axis of the plunger, bending of the plunger during operation is minimized, binding of the sensor is minimized, and a need for software to compensate for off-axis errors can be reduced or eliminated.

A first embodiment of the present disclosure and subject matter hereof provides a syringe pump that is capable of mechanically aligning a force sensor with an axis of a plunger of a syringe for a purpose of minimizing force measurement inaccuracies. In an embodiment, the syringe pump includes a syringe pump housing, a plunger retainer mechanism, and a syringe drive mechanism. The syringe pump housing is configured to receive at least a portion of the syringe, wherein the syringe is selected from a plurality of syringes of different dimensions. The plunger retainer mechanism is pivotably coupled to the syringe pump housing and configured to retain the plunger of the syringe. The plunger retainer mechanism is capable of pivoting relative to the syringe pump housing based on a sensed dimension of the plunger to align a force sensor coupled to the plunger retainer mechanism with the axis of the plunger. The syringe drive mechanism is operably coupled to the syringe pump housing and is configured to shift the plunger relative to a barrel of the syringe, thereby administering a medicament from the syringe.

A second embodiment of the present disclosure and subject matter hereof includes a syringe pump housing, a plunger retainer mechanism, and a syringe drive mechanism. The plunger retainer mechanism includes a force sensor that is shiftably coupled to the plunger retainer mechanism, thereby enabling movement of the force sensor along a linear path relative to the plunger retainer mechanism to align the force sensor with the axis of a plunger in a barrel of a syringe that is installed in or on the syringe pump housing.

A third embodiment of the present disclosure and subject matter hereof includes a syringe pump housing, a plunger retainer mechanism, and a syringe drive mechanism. The plunger retainer mechanism includes a force sensor and one or more thumb press captures. In this embodiment, the force sensor is operably coupled to the one or more thumb press captures, so that when the force sensor shifts along a linear path relative to the plunger retainer mechanism to align the force sensor with the axis of a plunger in a barrel of a syringe that is installed in or on the syringe pump housing, the one or more thumb press captures pivot relative to the plunger retainer mechanism to retain a thumb press of the plunger of the syringe. In this embodiment, the force sensor is substantially aligned with the axis of the plunger when the one or more thumb press captures abut the thumb press of the plunger of the syringe.

The summary above is not intended to describe each illustrated embodiment or every implementation of the present disclosure and subject matter hereof. The figures and the detailed description that follow more particularly exemplify these embodiments.

BRIEF DESCRIPTION OF THE DRAWINGS

The disclosure and subject matter hereof can be more completely understood in consideration of the following detailed description of various embodiments of the disclosure and subject matter hereof, in connection with the accompanying drawings, in which:

FIG. 2 is a schematic view depicting a syringe pump in accordance with an embodiment of the disclosure.

Figure 1:
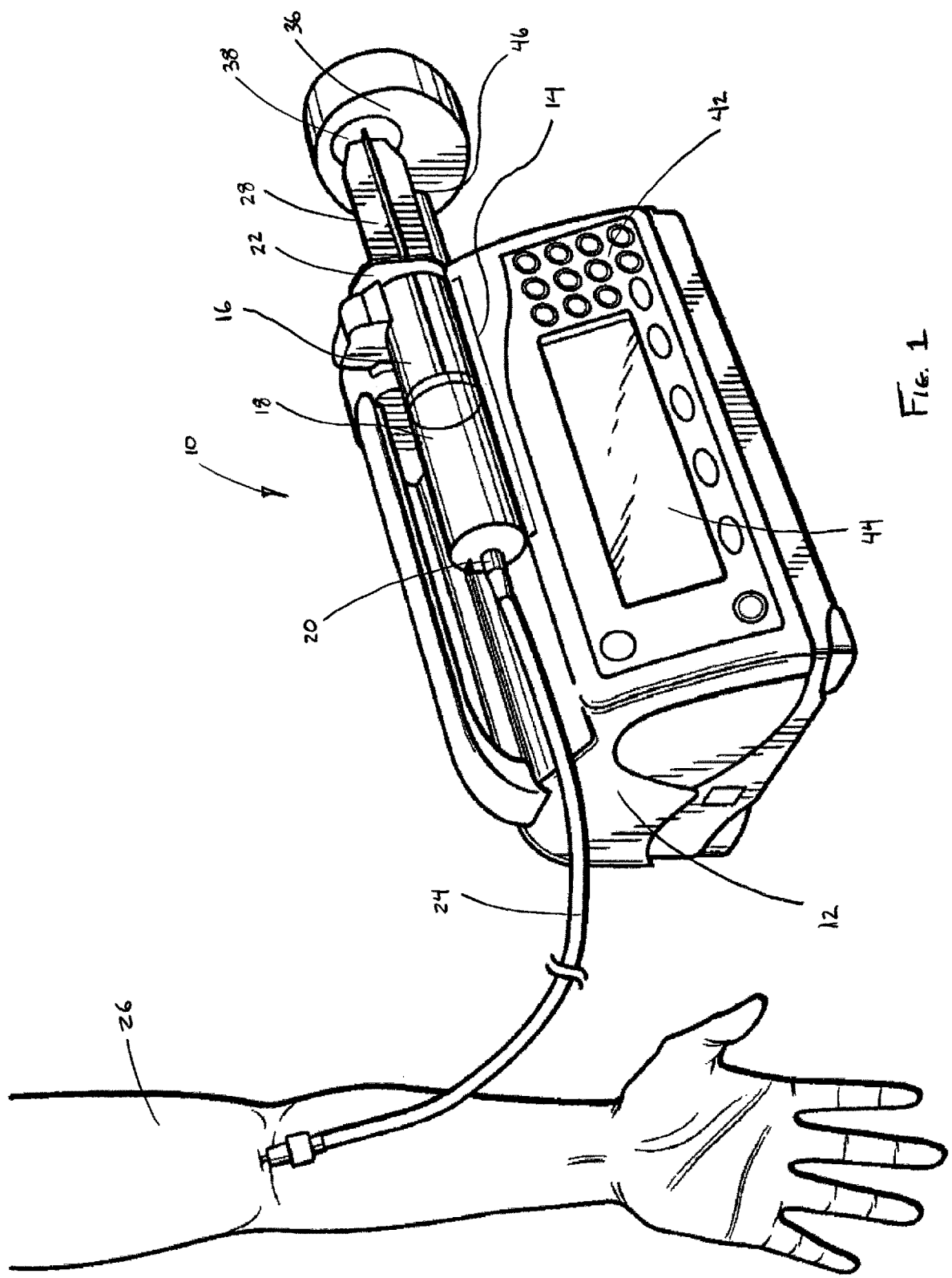
FIG. 1 is a perspective view depicting a syringe pump in accordance with an embodiment of the disclosure.

While embodiments of the disclosure are amenable to various modifications and alternative forms, specifics thereof are shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure as defined by the appended claims.

DETAILED DESCRIPTION

Referring to FIGS. 1-2, syringe pumps 10 (collectively, pump 10) in accordance with an embodiment of the disclosure are depicted. Pump 10 includes an outer housing 12 with a cradle, nest or recess 14 on a surface shaped to receive a syringe 16 of conventional kind. Syringe 16 has a cylindrical barrel 18 with an outlet or tip 20 at its forward end and a flange or ear 22 at its rear end. Tip 20 is connected to infusion tubing or line 24 so that medicament in syringe 16 can be dispensed to a patient 26 via infusion line 24.

Pump 10 has a syringe drive mechanism, such as including a lead screw 32 driven by a motor 34. The syringe drive mechanism is operably coupled to housing 12 and is configured to shift plunger 28 relative to cylindrical barrel 18, to controllably force medicament out tip 20 and into infusion line 24 so that medicament can be delivered to patient 26. In an embodiment, a syringe drive mechanism is coupled with a plunger retainer mechanism 36 for engaging a thumb press 38 of plunger 28. Motor 34 is driven by a control unit 40, which receives inputs from a keypad 42, or other user input means, and various sensors. Control unit 40 also provides an output to a display 44.

Figures 3A, 3B:
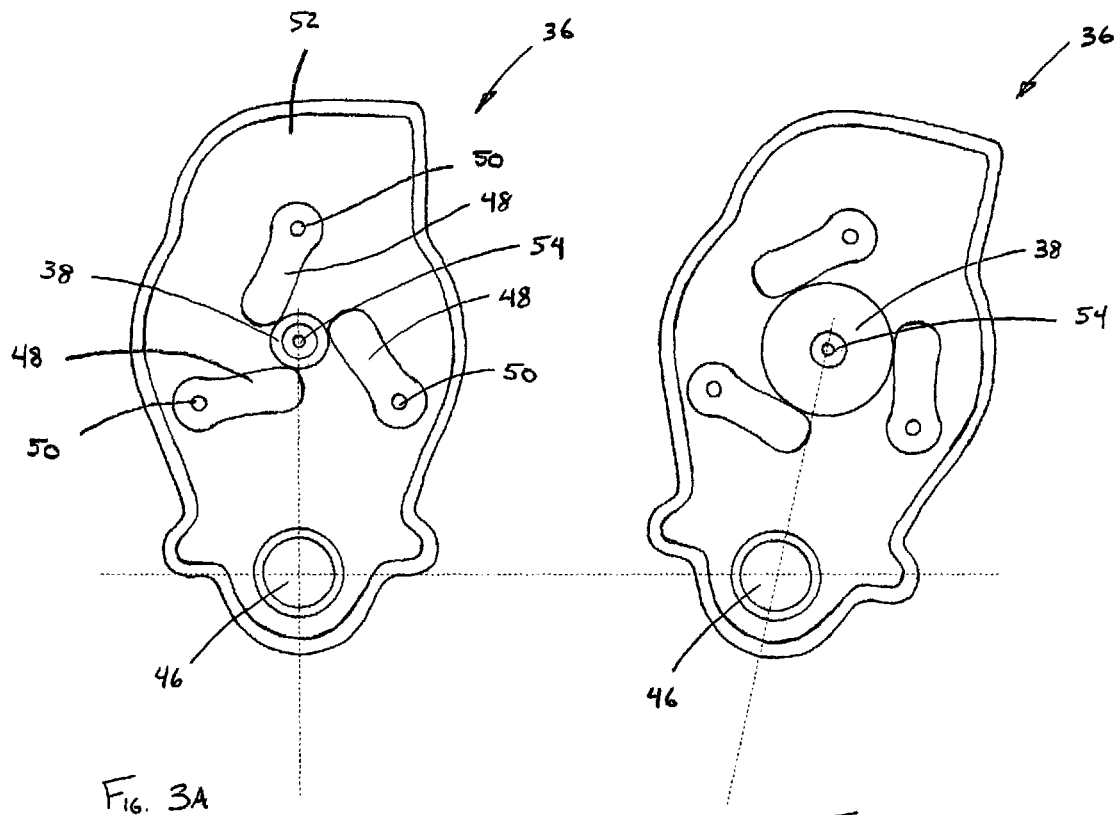
FIG. 3A is a plan view depicting a plunger retainer mechanism in accordance with a first embodiment of the disclosure, wherein arms of the plunger retainer mechanism are engaging a relatively small diameter syringe.
FIG. 3B is a plan view depicting the plunger retainer mechanism of FIG. 3A, wherein the arms are engaging a relatively large diameter syringe.

Referring to FIGS. 3A-3B, a plunger retainer mechanism 36 in accordance with a first embodiment of the disclosure and subject matter hereof is depicted. In an embodiment, plunger retainer mechanism 36 is pivotably coupled to syringe pump housing 12 by pivot mount 46. Plunger retainer mechanism 36 includes a frame 52 supporting one or more arms 48 each pivotably mounted to frame 52 by a pivot 50. For instance, as depicted in FIGS. 3A-3B, plunger retainer mechanism 36 can include three arms 48. In other embodiments, the plunger retainer mechanism 36 can include one, two, four, or any number of arms 48. In an embodiment, arms 48 are configured to pivot so as to abut a portion of a syringe 16 (not depicted in FIGS. 3A-3B) when syringe 16 is installed in or coupled to syringe pump 10 or otherwise loaded or positioned in recess 14 of pump 10 (as depicted in FIGS. 1 and 2), For example, in an embodiment, arms 48 are configured to pivot to removably but securely engage plunger 28 and/or thumb press 38, thereby removably but securely coupling plunger 28 and/or thumb press 38 to plunger retainer mechanism 36.

In an embodiment, plunger retainer mechanism 36 includes at least one force sensor 54. Force sensor 54 can be, for instance, a model FX1901 Force Sensor, available from Measurement Specialties, 1000 Lucas Way, Hampton, Va. 23666 www.meas-spec.com. Generally, sensors of this type are constructed from either a thin foil material or a glass substrate that has been metalized, such as a silicon wafer. In an embodiment, force sensor 54 is centrally located between arms 48 and pivots 50. For instance, force sensor 54 can be positioned at substantially equal distance from each pivot 50.

Figure 5:
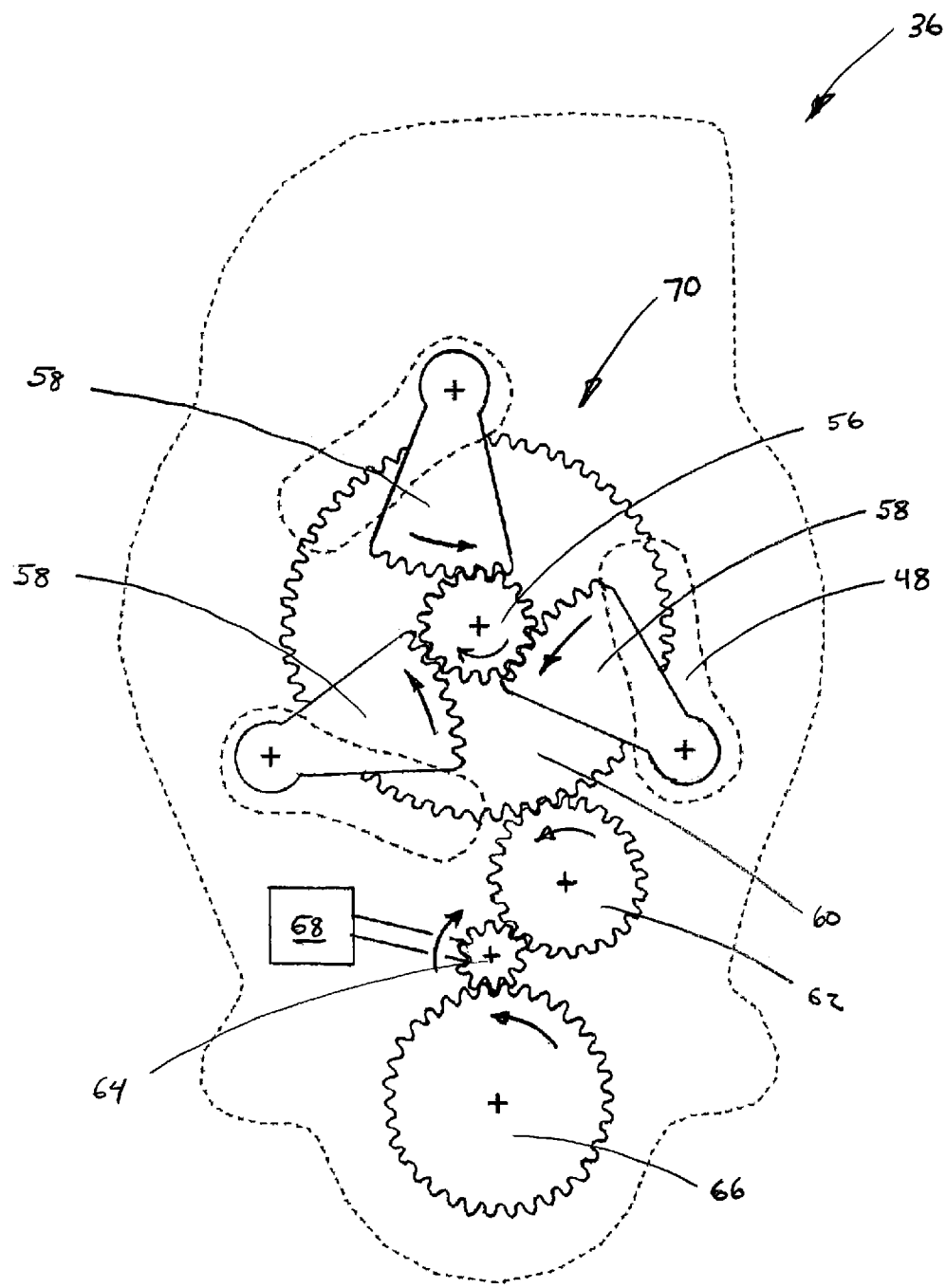
FIG. 5 is a plan view depicting a gear assembly of a plunger retainer mechanism in accordance with a first embodiment of the disclosure.

In an embodiment, arms 48 are operably coupled to one another, so that when more than one arm 48 is included in plunger retainer mechanism 36, arms 48 pivot in unison to cooperatively and correspondingly engage various portions of plunger 28 and/or thumb press 38 and thereby retain plunger 28 and/or thumb press 38 at multiple points around a perimeter of syringe 16, while ensuring that plunger 28 is axially aligned with force sensor 54. In an embodiment, this is accomplished through a so-called sun and planetary gear system. For instance, as depicted in FIG. 5, each arm 48 is fixedly coupled to a segment planetary gear 58 which interacts with a central sun gear 56. Accordingly, arms 48 are configured to grip a range of sizes or diameters of syringe plungers 28 and/or thumb presses 38. For instance, in an embodiment, plunger retainer mechanism 36 is configured to retain syringes 16 (not depicted in FIG. 5) having an internal volume of between 1 mL and 60 mL.

Figure 4:
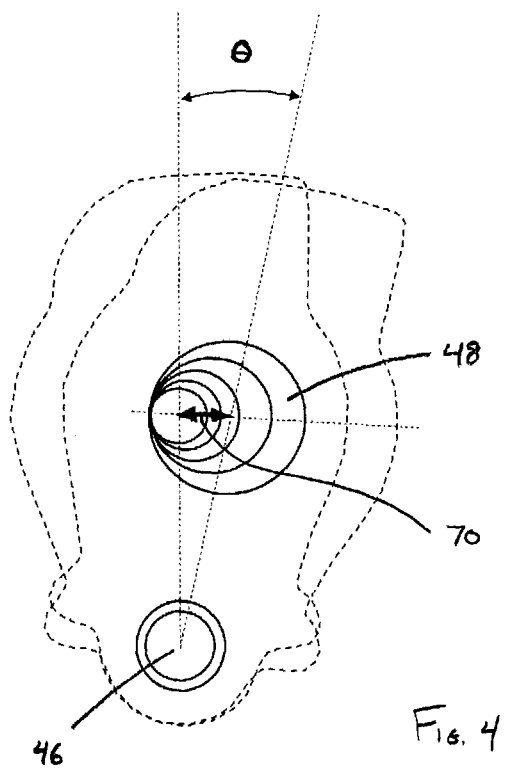
FIG. 4 is a schematic view depicting the plunger retainer mechanism of FIGS. 3A-B throughout a range of motion to accommodate syringes of varying diameters or sizes.

In an embodiment, arms 48 are operably coupled with pivot mount 46, such that when arms 48 pivot, plunger retainer mechanism 36 pivots with respect to syringe pump housing 12. By coupling the pivoting of arms 48 with the pivoting of plunger retainer mechanism 36, arms 48 can constrict around plunger 28 and or thumb press 38, while enabling syringe 16 to remain axially aligned in recess 14. In an embodiment, this is accomplished through a series of gears. For instance, as depicted in FIG. 5, sun gear 56 can be fixedly coupled to a larger diameter gear 60, which can interact with a series of gears 62, 64, and 66 to pivot plunger retainer mechanism 36 about pivot mount 46. Accordingly, as depicted in FIG. 4, in an embodiment, plunger retainer mechanism 36 can vary its angular position relative to an axial alignment of syringe 16 in recess 14 along an angle θ to thus maintain a desirable coaxial alignment of syringe 16, recess 14 and force sensor 54 throughout a range of sizes and diameters of syringes 16 installed in pump 10 (not depicted in FIG. 4). For example, in an embodiment, angle θ can be substantially equal to 14.23 degrees, thereby enabling force sensor 54 to traverse an arc representing an axial center of plunger 28 resulting from a range of syringe diameters or sizes. In an embodiment, the arc can measure approximately 0.5 inches in length.

Referring again to FIG. 5, collectively, gears 56, 58, 60, 62, 64, and 66 can be referred to as a gear assembly 70. Accordingly, gear assembly 70 enables plunger retainer mechanism 36 to rotatably align itself with an axial center of syringe 16 as it grips plunger 28 and/or thumb press 38 for retention in pump 10, thereby ensuring that force sensor 54 is coaxially aligned with forces applied by the syringe drive mechanism to plunger 28 during operation. In an embodiment, gear assembly 70 can be operably coupled with a motor, an actuator, or a manual drive mechanism 68 to actively pivot arms 48 and plunger retainer mechanism 36 into an intended position. The drive mechanism can cease driving gear assembly 70 when arms 48 contact plunger 28 and/or thumb press 38 of syringe 16. For instance, in an embodiment, when resistance of arms 48 against plunger 28 and/or thumb press 38 is sensed, the drive mechanism ceases driving gear assembly 70.

In operation, when syringe 16 is installed in syringe pump 10, the drive mechanism will be in an extended position (away from housing 12 of pump 10, or toward a right side of FIGS. 1 and 2) and plunger retainer mechanism 36 will be rotated about pivot mount 46 to an open position. Thus, arms 48 of plunger retainer mechanism 36 are positioned by way of gear assembly 70 to minimize interference with plunger 28 and/or thumb press 38 as syringe 16 is loaded or installed in pump 10. When syringe 16 is then loaded or installed in recess 14 of housing 12 of pump 10, plunger retainer mechanism 36 is rotated to a retention position until resistance of arms 48 against plunger 28 and/or thumb press 38 is sensed. This causes arms 48 to grip a portion of plunger 28 and/or thumb press 38 as aforedescribed, while assisting to keep barrel 18 of syringe 16 aligned with recess 14. In some embodiments, pressing a load button on keypad 42 causes the drive mechanism to actively pivot arms 48 and plunger retainer mechanism 36 into a retention position, thereby ensuring that force sensor 54 is axially aligned with plunger 28. In another embodiment, plunger retainer mechanism 36 is moved manually or by other means. The syringe drive mechanism is adjusted as necessary to ensure proper loading or installing of syringe 16 in pump 10.

When removing syringe 16 from pump 10, the syringe drive mechanism is rotated in an opposite direction, thereby pivoting arms 48 to release a portion of plunger 28 and/or thumb press 38 that had been retained between arms 48 and plunger retainer mechanism 36. Syringe 16 can then be removed from recess 14.

Figure 6:
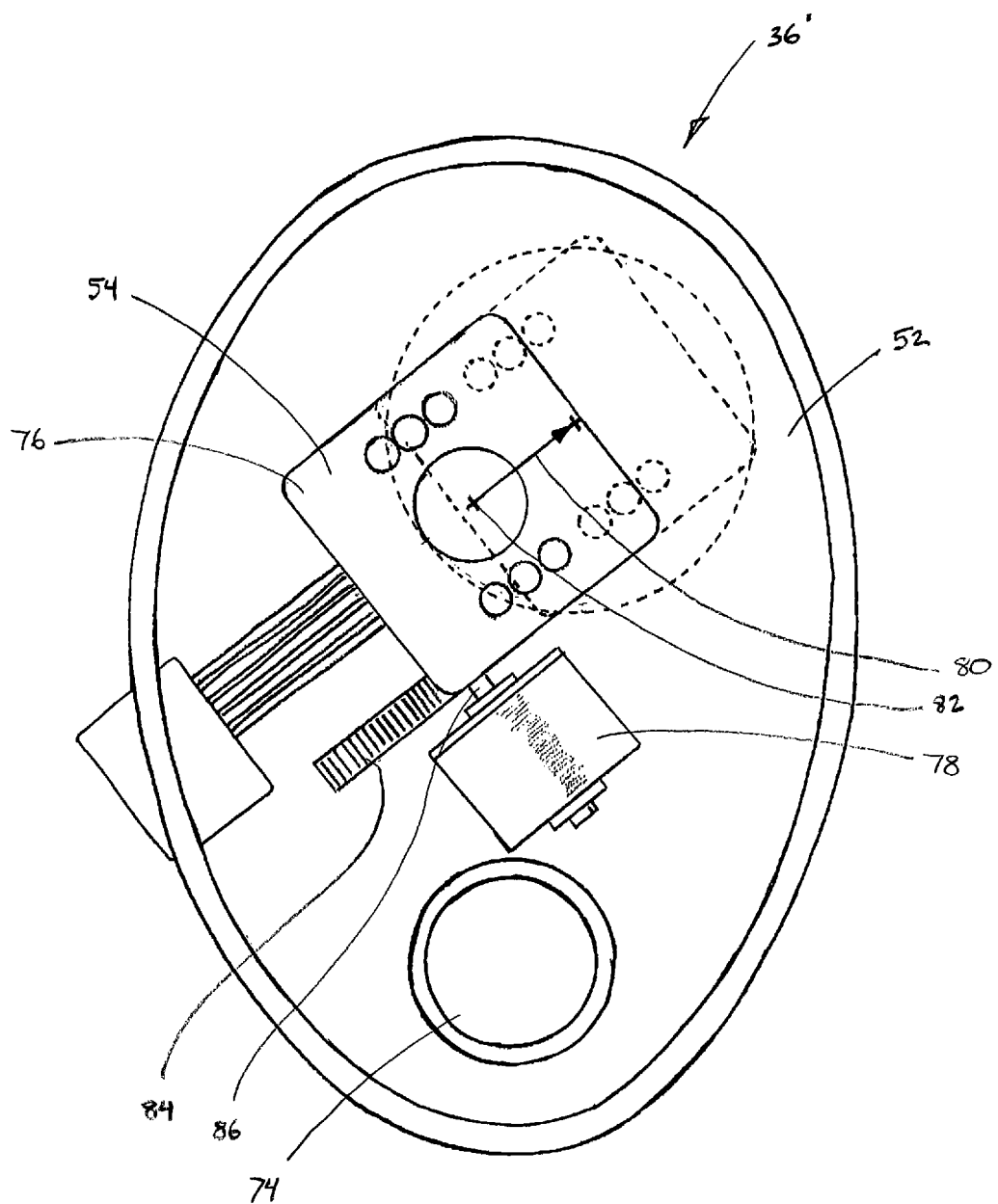
FIG. 6 is a plan view depicting a plunger retainer mechanism in accordance with a second embodiment of the disclosure.

Referring to FIG. 6, a plunger retainer mechanism 36' in accordance with a second embodiment of the disclosure and subject matter hereof is depicted. In this embodiment, plunger retainer mechanism 36' is operably coupled to syringe pump housing 12 by mount 74; however, unlike the first embodiment plunger retainer mechanism 36, this second embodiment of plunger retainer mechanism 36' need not pivot with respect to syringe pump housing 12. Instead, in this embodiment, to enable alignment with plunger 28 of a range of syringe diameters or sizes, force sensor 54 is shiftable along a linear path 80.

In this second embodiment, plunger retainer mechanism 36' includes a frame 52 supporting a movable element 76 and a drive mechanism 78. In an embodiment, moveable element 76 is operably coupled to frame 52 by a slideable connector, such as a track and clip assembly (not depicted), that enables moveable element 76 to traverse along a substantially linear path 80 relative to frame 52. In an embodiment, drive mechanism 78 can be a motor, for example, a stepper motor. Movable element 76 can include a toothed rack 84 for interaction with a pinion gear 86 coupled to drive mechanism 78, thereby enabling element 76 to be driven forwardly or backwardly into a desired position 82 along linear path 80. Force sensor 54 can be fixedly coupled to movable element 76, thereby enabling axial alignment of plunger 28 (not depicted in FIG. 6) of a range of syringe diameters or sizes, with force sensor 54 along linear path 80.

Figure 7:
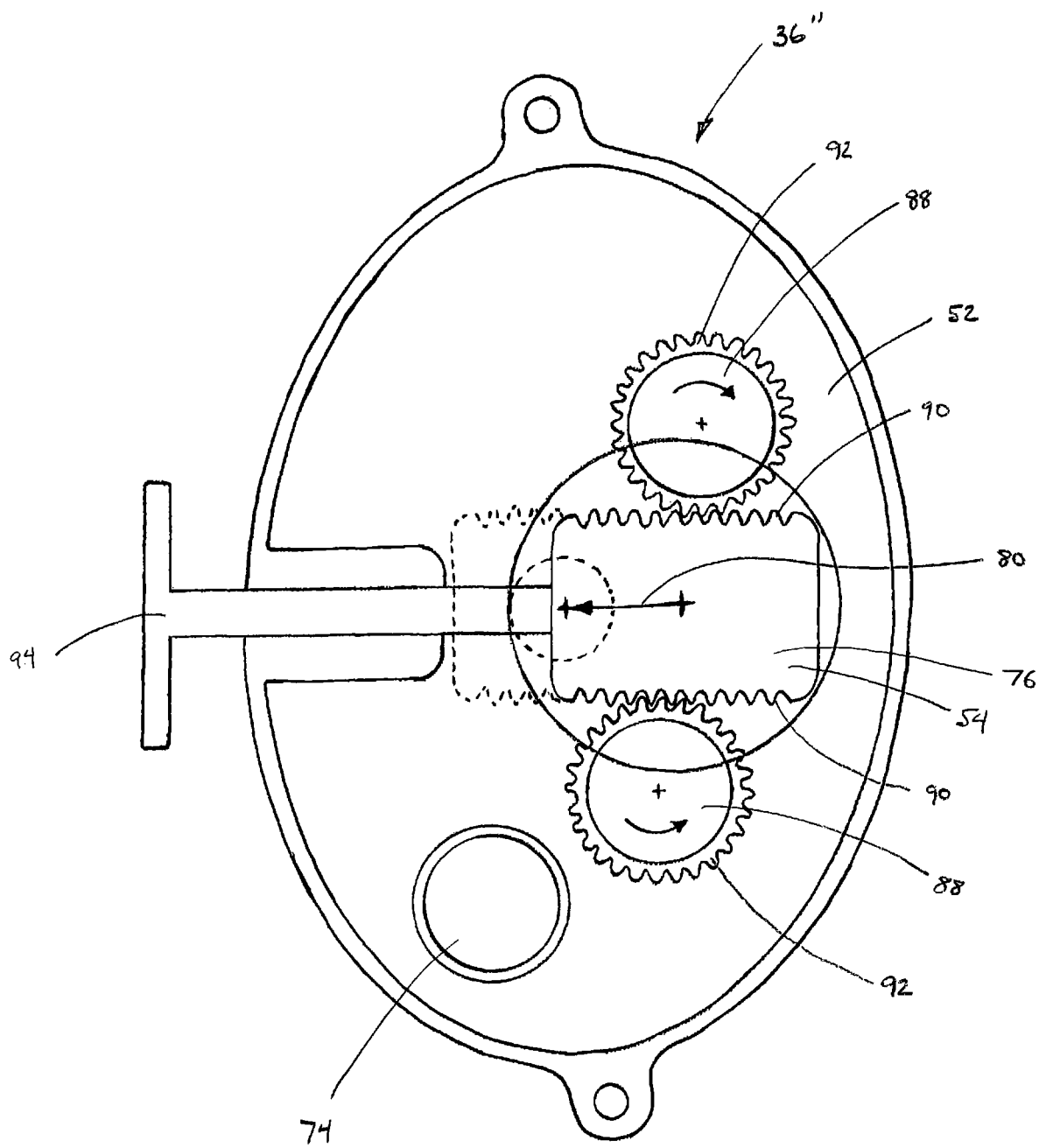
FIG. 7 is a plan view depicting a plunger retainer mechanism in accordance with a third embodiment of the disclosure.

Referring to FIG. 7, a plunger retainer mechanism 36" in accordance with a third embodiment of the disclosure and subject matter hereof is depicted. In this embodiment, and analogously to the second embodiment, plunger retainer mechanism 36" can be non-pivotably coupled to syringe pump housing 12 by mount 74, and force sensor 54 can be shiftable along a linear path 80.

In this third embodiment, plunger retainer mechanism 36" includes a frame 52 supporting a movable element 76, driven by one or more pivotable syringe plunger thumb press captures 88. Moveable element 76 is operably coupled to frame 52 by a slideable connector, such as a track and clip assembly (not depicted), that enables moveable element 76 to traverse along a substantially linear path 80 relative to frame 52. Each thumb press capture 88 can rotate about pivot 50 relative to frame 52 and can include one or more arms 48 (not explicitly depicted in FIG. 7, but as depicted analogously in FIG. 3A). In an embodiment, arms 48 are configured to pivot to removably but securely engage plunger 28 and/or thumb press 38 of syringe 16 (not depicted in FIG. 7), thereby removably but securely coupling plunger 28 and/or thumb press 38 to plunger retainer mechanism 36".

Movable element 76 can include one or more toothed racks 90 for interaction with a plurality of teeth 92 at least partially surrounding pivot 50 (again, not explicitly depicted in FIG. 7; but as depicted analogously in FIG. 3A), thereby causing each thumb press capture 88 to pivot relative to frame 52 as moveable element 76 traverses forwardly or backwardly along linear path 80. Force sensor 54 can be fixedly coupled to movable element 76, thereby enabling axial alignment of plunger 28 (not depicted in FIG. 7) of a range of syringe diameters or sizes, with force sensor 54 along linear path 80. As moveable element 76 traverses along linear path 80 to align the force sensor 54 with the plunger 28, each thumb press capture 88 pivots relative to frame, so as to securely engage plunger 28 and/or thumb press 38 by way of one or more arms 48 (again, not explicitly depicted in FIG. 7) as aforedescribed.

In an embodiment, a push rod 94 enables control of the position of movable element 76 along linear path 80. In an embodiment, push rod 94 is controlled manually by a user. In other embodiments, push rod 94 is controlled by one or more drive mechanisms, such as a motor or actuator (not depicted). In other embodiments, push rod 94 is mechanically or electro-mechanically linked to components (not depicted) in syringe pump 10 that move in response to varying sizes of syringes 16 installed in pump 10.

Persons of ordinary skill in the relevant arts will recognize that embodiments may comprise fewer features than illustrated in any individual embodiment described above. Embodiments described by example or otherwise contemplated herein are not meant to be an exhaustive presentation of ways in which the various features may be combined, substituted, or arranged. Accordingly, the embodiments are not mutually exclusive combinations of features; rather, embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

It is therefore also to be appreciated and understood that, irrespective of a particular embodiment, the novel and inventive subject matter hereof—as described by example or otherwise contemplated herein—advantageously provides controlled movement of a force sensor of a syringe pump to maintain axial alignment of the force sensor with a component or components of a medicament reservoir (such as, for example, a thumb press of a syringe) installed in the pump. Such alignment of the force sensor with an axis or centerline of the reservoir can advantageously reduce, or even in some instances eliminate, an offset between the axes of the force sensor and the reservoir. Thus, any discrepancy between an actual force applied by the pump on the reservoir and a value of a measured force experienced by the force sensor can be reduced or possibly eliminated. Furthermore, such controlled movement of the force sensor into axial alignment with medicament reservoirs of varying diameters can aid in minimizing start-up delays that otherwise would typically occur with known syringe pumps where the force sensor is fixed in one location. Additional advantages of such a controllably moveable force sensor can include, for example: minimizing or eliminating a need for algorithmic compensation to account for force sensor discrepancies in a pump start-up routine, etc.; more reliable and direct force sensor operations and measurements; reduced bending moments that could otherwise be experienced by reservoir components due to off-axis driving forces from the pump; and minimizing or eliminating a desire to move the reservoir or syringe itself, installed in the pump, to be in better axial alignment with the force sensor.

Any incorporation by reference of documents above is limited such that no subject matter is incorporated that is contrary to the disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

The invention claimed is:

1. A syringe pump configured to mechanically align a force sensor with an axis of a plunger of a syringe for a purpose of minimizing force measurement inaccuracies, comprising:
   a syringe pump housing configured to receive at least a portion of the syringe, wherein the syringe is selected from a plurality of syringes of different dimensions;
   a plunger retainer mechanism pivotably coupled to the syringe pump housing and configured to retain the plunger of the syringe, wherein the force sensor is operably coupled to the plunger retainer mechanism and pivots relative to the syringe pump housing based on a sensed dimension of the plunger to align the force sensor with the axis of the plunger; and
   a syringe drive mechanism operably coupled to the syringe pump housing and configured to shift the plunger relative to the portion of the syringe received by the syringe pump housing.

2. The syringe pump of claim 1, wherein the plunger retainer mechanism includes at least one arm configured to pivot so as to abut a portion of the syringe.

3. The syringe pump of claim 2, wherein the plunger retainer mechanism includes three arms.

4. The syringe pump of claim 2, wherein the plunger retainer mechanism includes a gear assembly configured to pivot the at least one arm into contact with the syringe.

5. The syringe pump of claim 4, wherein the gear assembly is driven by a drive mechanism.

6. The syringe pump of claim 5, wherein the drive mechanism is a motor.

7. The syringe pump of claim 6, wherein the motor is at least partially controlled by a keypad.

8. A syringe pump configured to mechanically align a force sensor with an axis of a plunger of a syringe for a purpose of minimizing force measurement inaccuracies, comprising:

a syringe pump housing configured to receive at least a portion of the syringe, wherein the syringe is selected from a plurality of syringes of different dimensions;

a plunger retainer mechanism coupled to the syringe pump housing and configured to retain the plunger of the syringe, wherein the force sensor is shiftably coupled to the plunger retainer mechanism enabling movement of the force sensor along a linear path relative to the plunger retainer mechanism to align the force sensor with the axis of the plunger; and a syringe drive mechanism operably coupled to the syringe pump housing and configured to shift the plunger relative to the portion of the syringe received by the syringe pump housing.

9. The syringe pump of claim 8, wherein the force sensor is mounted to a toothed rack.

10. The syringe pump of claim 9, wherein the toothed rack is driven by a drive mechanism.

11. The syringe pump of claim 10, wherein the drive mechanism is a pushrod.

12. The syringe pump of claim 10, wherein the drive mechanism is a motor.

13. The syringe pump of claim 12, wherein the motor is at least partially controlled by a keypad.

14. The syringe pump of claim 8, wherein the plunger retainer mechanism includes at least one arm configured to pivot so as to abut a portion of the syringe.

15. The syringe pump of claim 14, wherein the plunger retainer mechanism includes a gear assembly configured to pivot the at least one arm into contact with the syringe.

* * * * *